United States Patent [19]

Paget

[11] 4,075,218

[45] Feb. 21, 1978

[54] s-TRIAZOLO[5,1-b]BENZOTHIAZOLES

[75] Inventor: Charles J. Paget, Indianapolis, Ind.

[73] Assignee: Eli Lilly and Company, Indianapolis, Ind.

[21] Appl. No.: 682,007

[22] Filed: May 3, 1976

Related U.S. Application Data

[62] Division of Ser. No. 547,828, Feb. 7, 1975, Pat. No. 3,974,286.

[51] Int. Cl.$^2$ .................................... C07D 277/82
[52] U.S. Cl. ........................................... 260/305
[58] Field of Search ................................ 260/305

[56] References Cited

U.S. PATENT DOCUMENTS

| | | | |
|---|---|---|---|
| 3,389,137 | 6/1968 | Mosby et al. | 260/256.4 |
| 3,639,406 | 2/1972 | Reimlinger et al. | 260/288 |
| 3,764,681 | 10/1973 | Dreikorn | 424/258 |
| 3,775,417 | 11/1973 | de Ruiter et al. | 260/288 R |
| 3,839,569 | 10/1974 | Dreikorn et al. | 424/258 |
| 3,937,713 | 2/1976 | Paget et al. | 424/270 X |

FOREIGN PATENT DOCUMENTS 803,098 3/1973 Belgium.
2,249,350 4/1974 Germany.

OTHER PUBLICATIONS

Tamura et al., J. Hetero Chem X, 947–951, (1973).
Shiho et al., J. Am. Chem. Soc. 82, 4044–4054, (1960).
Potts et al., J. Org. Chem. 36, 10-13, (1971).
Saburo et al., Chem. Abst. 75, (1971), 140863g.
Koshel et al., Khimiya Geterotskilicheskikh Soedinenii, 6, 851-854, (1970).

*Primary Examiner*—Allen J. Robinson
*Attorney, Agent, or Firm*—William E. Maycock; Joseph A. Jones; Everet F. Smith

[57] ABSTRACT

A class of s-triazolo[5,1-b]benzothiazoles are disclosed and are shown to be useful for the control of foliage-consuming insects and fungi which attack the foliage of plants.

9 Claims, No Drawings s-TRIAZOLO[5,1-b]BENZOTHIAZOLES

This is a division of application Ser. No. 547,828, filed Feb. 7, 1975, now U.S. Pat. No. 3,974,286.

BACKGROUND OF THE INVENTION

This invention relates to the field of agricultural chemistry, and provides to the art new compounds which control harmful insects and phytopathogens.

Agricultural chemistry has long attempted to improve on existing insecticides and fungicides. Many classes of organic compounds have been used, and new compounds are constantly being made and evaluated. Some of the prior art has a relationship to the present invention.

Dreikorn, U.S. Pat. Nos. 3,764,681 and 3,839,569, disclosed the fungicidal efficacy of tetrazolo[1,5-a]quinolines and s-triazolo[4,3-a]quinolines. Belgian Patent 803,098 and West German Offenlegungsschrift No. 2,249,350 disclosed that certain imidazoquinoxalines are also useful as agricultural fungicides.

Paget, U.S. patent application Ser. No. 296,380, filed Oct. 10, 1972 now abandoned, disclosed fungicidal methods making use of s-triazolo[3,4-b]benzothiazoles.

Tamura et al., "Novel Syntheses of Thiazolo[3,2-b]-s-Triazoles", Hetero. Chem. X, 947-51 (1973), published February 16, 1974, disclosed one of the compounds here described.

Potts et al., "Synthesis of the Thiazolo[2,3-c]-s-Triazole and the Thiazolo[3,2-b]-s-Triazole Systems", J. Org. Chem. 36, 10-13 (1971), and Japanese Patent 71 26,500, C.A. 75, 140863(g) (1971) disclosed thiazolo[3,2-b]-s-triazoles, which were said to be useful as bactericides and agricultural chemicals.

Mosby et al., U.S. Pat. No. 3,389,137, showed a tetrazolo[5,1-b]benzothiazole, which was described only as an intermediate to phosphene imide compounds.

SUMMARY

The compounds of this invention are of the formula

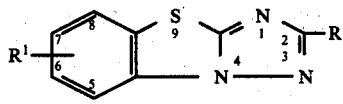

wherein R represents
  hydrogen,
  hydroxy,
  trifluoromethyl,
  methyl, or
  ethyl;
$R^1$ represents
  hydrogen,
  methyl,
  ethyl,
  chloro,
  propyl,
  fluoro,
  isopropyl,
  bromo, or
  methoxy;
provided that when R represents ethyl or trifluoromethyl, $R^1$ represents methyl or ethyl; and provided that methoxy, propyl and isopropyl $R^1$ groups occupy only the 5-position.

A preferred group of compounds comprises the compounds of the above formula wherein R represents hydrogen.

The preferred $R^1$ substituents are hydrogen, methyl, ethyl, chloro and fluoro, and the preferred location for the $R^1$ substituents is the 5-position.

Important embodiments of the invention are the methods for reducing the adverse effects of foliage-attacking fungi and of foliage-consuming insects disclosed herein. The method for reducing the adverse effects of such fungi comprises contacting the fungi with a compound of the above formula wherein R represents methyl, hydroxy or hydrogen.

The method of reducing the adverse effects of foliage-consuming insects comprises contacting the insects with a compound of the above formula wherein R represents methyl, ethyl, trifluoromethyl or hydrogen, provided that when R represents a group other than hydrogen, $R^1$ represents hydrogen, methyl, ethyl or chloro.

DESCRIPTION OF THE PREFERRED EMBODIMENT

The compounds below are typical of the compounds of the present invention. It will be understood that the named compounds do not bound the scope of the invention, but are named merely to assure that agricultural chemists will fully understand the invention.
  6-chloro-s-triazolo[5,1-b]benzothiazole
  5-bromo-2-hydroxy-s-triazolo[5,1-b]benzothiazole
  7-fluoro-2-hydroxy-s-triazolo[5,1-b]benzothiazole
  8-bromo-2-methyl-s-triazolo[5,1-b]benzothiazole
  6-ethyl-s-triazolo[5,1-b]benzothiazole
  2-ethyl-7-methyl-s-triazolo[5,1-b]benzothiazole
  7-ethyl-2-hydroxy-s-triazolo[5,1-b]benzothiazole
  6-methyl-2-trifluoromethyl-s-triazolo[5,1-b]benzothiazole
  8-methyl-2-trifluoromethyl-s-traizolo[5,1-b]benzothiazole
  5-methoxy-2-hydroxy-s-triazolo[5,1-b]benzothiazole
  5-propyl-s-triazolo[5,1-b]benzothiazole
  5-isopropyl-2-methyl-s-triazolo[5,1-b]benzothiazole
  7-chloro-s-triazolo[5,1-b]benzothiazole
  7-bromo-s-triazolo[5,1-b]benzothiazole
  8-fluoro-s-triazolo[5,1-b]benzothiazole
  7-ethyl-2-methyl-s-triazolo[5,1-b]benzothiazole
  2-methyl-5-propyl-s-triazolo[5,1-b]benzothiazole
  2-hydroxy-5-isopropyl-s-triazolo[5,1-b]benzothiazole
  7-ethyl-2-trifluoromethyl-s-triazolo[5,1-b]benzothiazole
  2,6-diethyl-s-triazolo[5,1-b]benzothiazole The preferred compounds of this invention are 5-methyl-s-triazolo[5,1-b]benzothiazole, 5-fluoro-s-triazolo[5,1-b]benzothiazole, s-triazolo[5,1-b]benzothiazole, 5-chloro-s-triazolo[5,1-b]benzothiazole, 5-methoxy-s-triazolo[5,1-b]benzothiazole, and 2,5-dimethyl-s-triazolo[5,1-b]benzothiazole.

The compounds of this invention are made from 2-aminobenzothiazoles, which are readily obtained. The $R^1$ substituents of the compounds are provided by corresponding substituents on the starting 2-aminobenzothiazoles.

Various processes for the synthesis of the new compounds can be used. Tamura, cited above, taught a process which began with the preparation of 3-amino-2-iminobenzothiazoline, which he described as a 2,3-diamino compound, by the reaction of the 2-aminobenzothiazole compound with O-mesitylenesulfonylhydroxylamine at ice bath temperature in methylene dichloride. The amino-imino compound, produced as the mesitylene sulfonate salt, was refluxed with acetic anhydride to produce 2-methyl-s-triazolo[5,1-b]benzothiazole in 80 percent yield.

The Tamura process is functional, but produces the 2-acetylamino-3-acetylimino compound as a side product.

The best route for the preparation of the compounds wherein R represents methyl or ethyl proceeds by the cyclization with polyphosphoric acid of an intermediate 2-alkanoylimino-3-aminobenzothiazoline.

The intermediate is prepared by the reaction with O-mesitylenesulfonylhydroxylamine of a 2-aminobenzothiazole, in an aromatic solvent or a halogenated solvent such as methylene dichloride at a temperature from the freezing point of the reaction mixture to room temperature, preferably ice bath temperature, to produce a 3-amino-2-imino compound as the mesitylene sulfonate salt. The salt is converted to the free base by treatment with a strong base, and the free base reacted with acetyl or propionyl halide to produce the acylated intermediate. The acylation is done at the same temperature as the amination step in an aromatic, alkane or halogenated solvent, or in an ether such as tetrahydrofuran, in the presence of an acid scavenger such as triethylamine, or other tertiary amines, or a strong inorganic base such as an alkali metal carbonate.

The cyclization of the intermediate is carried out in neat polyphosphoric acid. The reaction goes most efficiently at relatively high temperatures such as from 100° to 120° C., at which temperatures the reaction goes in good yields in about 1 to 2 hours.

Compounds wherein R represents trifluoromethyl are produced by the same general process, acylating the 3-amino-2-imino compound with trifluoroacetic anhydride.

The compounds wherein R represents hydrogen are conveniently made by cyclizing an intermediate 3-imino-2-iminobenzothiazoline with triethylorthoformate in an inert reaction solvent. Xylene is the preferred solvent, but other aromatic solvents are also useful. The mixture is heated slowly, and the ethanol released by the reaction should be removed by the use of a Dean-Stark trap or a similar device on the reaction flask. Compounds having a 2-methyl group can be made in the same way by using triethylorthoacetate in place of triethylorthoformate.

Compounds wherein R represents hydrogen are also made by cyclizing the amino-imino salt intermediate with neat formic acid at reflux temperature for 12-24 hours.

The compounds wherein R represents hydroxy are made by the cyclization of a 2-methoxycarbonylimino-3-aminobenzothiazoline. The intermediate is produced by acylating a 3-amino-2-imino compound with chloroformic acid, methyl ester, in the usual fashion. The intermediate is cyclized either thermally, at the melting point neat, or by treatment with an alkali metal hydride in an inert solvent such as an ether, an alkane, or an aromatic solvent, preferably tetrahydrofuran, at reflux temperature.

Another useful method of synthesis for the compounds begins with a 1-acyl-2-phenylhydrazine, which is reacted with an alkali metal thiocyanate in an aromatic solvent at an elevated temperature from 40° C. to reflux temperature. The intermediate product is a 4-acyl-3-phenylthiosemicarbazide, which is cyclized with bromine in a halogenated solvent at a temperature from about 30° C. to the reflux temperature of the reaction mixture to produce a 3-acylamino-2-iminobenzothiazoline as the HBr salt. The salt is reduced to the free base by contact with a strong base as described above, and is cyclized by heating at the reflux temperature in acetic acid to produce the desired product.

The following preparative examples illustrate the synthetic methods used in preparing the compounds of this invention. The first example shows the preparation of a typical 3-amino-2-imino intermediate compound.

EXAMPLE 1

3-amino-2-imino-4-methoxybenzothiazoline

A 7.2 g. portion of 2-amino-4-methoxybenzothiazole was slurried in methylene dichloride. The mixture was cooled in an ice bath, and an 11 g. portion of mesitylenesulfonylhydroxylamine was added, as a methylene dichloride solution at ice bath temperature. The reaction mixture was allowed to warm gradually to room temperature over a three hour period. The reaction mixture was then diluted with ethyl ether and filtered.

The solids were slurried in 100 ml. of chloroform. A solution of 6 g. of KOH in 75 ml. of water was added over a 30-minute period. The solid crude product was separated by filtration, and the chloroform layer was evaporated to dryness under vacuum to produce more product. The products were combined and recrystallized from ethyl acetate to produce 4.8 g. of 3-amino-2-imino-4-methoxybenzothiazoline, m.p. 131°-32° C. which was identified by nuclear magnetic resonance analysis.

The next three examples illustrate the acylation of 3-amino-2-imino intermediate compounds.

EXAMPLE 2

3-amino-4-methyl-2-propionyliminobenzothiazoline

A 3.6 g. portion of 3-amino-2-imino-4-methylbenzothiazoline was dissolved in about 100 ml. of tetrahydrofuran, and 2.2 g. of triethylamine was added. The reaction mixture was cooled in an ice bath, and 2 g. of propionyl chloride, dissolved in 2 ml. of tetrahydrofuran, was added dropwise while the mixture was stirred. After the addition was complete, the reaction mixture was stirred at ice bath temperature for about 3 hours, and was then diluted with an equal volume of water. The tetrahydrofuran was removed under vacuum, and the remaining aqueous mixture was filtered to recover the product. After recrystallization from ethanol, the yield of purified product was 3.2 g. of 3-amino-4-methyl-2-propionyliminobenzothiazoline, m.p. 175°-76° C. The product was identified by nuclear magnetic resonance and ultraviolet analysis and by elemental microanalysis.

|   | Theoretical | Found |
|---|---|---|
| C | 56.15% | 56.43% |
| H | 5.57 | 5.76 |
| N | 17.86 | 17.61 |

EXAMPLE 3

3-amino-4-methyl-2-trifluoroacetyliminobenzothiazoline

A 1.8 g. portion of 3-amino-2-imino-4-methylbenzothiazoline was slurried in about 50 ml. of tetrahydrofuran, and 1.5 g. of triethylamine was added. The reaction mixture was then cooled as above, and 2.3 g. of trifluoroacetic anhydride was added dropwise. The reaction mixture was stirred at ice bath temperature for about 4 hours after completion of the addition, and the reaction mixture was then worked up as described in Example 2. The product was not recrystallized, and the yield was 2.6 g. of 3-imino-4-methyl-2-trifluoroacetyliminobenzothiazoline, m.p. 160°–61° C. The elemental microanalysis was as follows

|   | Theoretical | Found |
|---|---|---|
| C | 43.60% | 43.29% |
| H | 2.91 | 2.93 |
| N | 15.25 | 15.00 |

EXAMPLE 4

3-amino-2-methoxycarbonylimino-4-methylbenzothiazoline

The reaction was carried out according to the process of Example 3, using 1.8 g. of the same starting compound and acylating with 1.04 g. of chloroformic acid, methyl ester, in the presence of 1.3 g. of triethylamine in 50 ml. of tetrahydrofuran. The product was identified by nuclear magnetic resonance and ultraviolet analysis, and by elemental microanalysis, as follows.

|   | Theoretical | Found |
|---|---|---|
| C | 50.62% | 50.86% |
| H | 4.67 | 4.91 |
| N | 17.71 | 17.66 |

The next example demonstrates the cyclization of acylated intermediates with polyphosphoric acid.

EXAMPLE 5

5-methyl-2-trifluoromethyl-s-triazolo[5,1-b]benzothiazole

A 2.2 g. portion of the intermediate product made in Example 3 was slurried in 15 ml. of polyphosphoric acid. The mixture was heated to about 110° C. for about 1½ hours. The mixture was then allowed to cool to room temperature, and was diluted with a large amount of water. The aqueous mixture was neutralized with $NH_4OH$ and filtered to separate the crude product. After recrystallizing from hexane, the yield was 0.92 g. of 5-methyl-2-trifluoromethyl-s-triazolo[5,1-b]benzothiazole, m.p. 80°–81° C. The elemental microanalysis of the product was as follows.

|   | Theoretical | Found |
|---|---|---|
| C | 46.69% | 46.77% |
| H | 2.35 | 2.47 |
| N | 16.34 | 16.44 |

The following example exemplifies the cyclization of a 2-hydroxy compound.

EXAMPLE 6

2-hydroxy-5-methyl-s-triazolo[5,1-b]benzothiazole

A 9.2 g. portion of 3-amino-2-methoxycarbonylimino-4-methylbenzothiazoline, produced by the process of Example 4, was heated in a flask in a Woods metal bath at approximately 220° C. for approximately 1½ hours. The flask was then allowed to cool, and the product was recrystallized from dimethylformamide to produce 5.9 g. of 2-hydroxy-5-methyl-s-triazolo[5,1-b]benzothiazole, m.p. higher than 300° C., the elemental microanalysis of which was as follows.

|   | Theoretical | Found |
|---|---|---|
| C | 52.67% | 52.62% |
| H | 3.44 | 3.59 |
| N | 20.47 | 20.33 |

Example 7 below is typical of cyclization reactions using triethylorthoformate or triethylorthoacetate as the reagent.

EXAMPLE 7

5-chloro-s-triazolo[5,1-b]benzothiazole

A 4 g. portion of 3-amino-4-chloro-2-iminobenzothiazoline was slurried in 50 ml. of xylene. To the mixture was added 3.7 g. of triethylorthoformate dissolved in about 10 ml. of xylene. The mixture was then heated very slowly to the reflux temperature. The ethanol which distilled from the mixture was collected in a Dean-Stark trap. After about 1 hour, the mixture was allowed to cool. The cooled reaction mixture was filtered, and the solids were washed with benzene. The yield was 2.8 g. of 5-chloro-s-triazolo[5,1-b]benzothiazole, m.p. 203°–05° C., which was identified by nuclear magnetic resonance analysis and elemental microanalysis.

|   | Theoretical | Found |
|---|---|---|
| C | 45.83% | 45.99% |
| H | 1.92 | 1.99 |
| N | 20.04 | 19.94 |

The following example shows the synthesis of a typical compound by the process starting with an acylphenylhydrazine.

EXAMPLE 8

2-methyl-s-triazolo[5,1b]benzothiazole

A 15 g. portion of 1-acetyl-2-phenylhydrazine was mixed with 75 ml. of benzene, and 16.4 g. of sodium thiocyanate was added. The reaction mixture was heated to 45° C., and 16 g. of trifluoroacetic acid was added. The mixture was then heated to reflux temperature, and stirred at that temperature for 3½ hours. Excess benzene was then decanted, and the thick residue was poured into water. An equal volume of ethyl acetate was added, and the solids were separated from the mixture by filtration and washed with ethyl acetate. The yield was 6.5 g. of 4-acetyl-3-phenylthiosemicarbazide, m.p. 194°–95° C.

The above intermediate product was slurried in 70 ml. of ethylene dichloride, and 5.3 g. of bromine dissolved in 30 ml. of ethylene dichloride was added dropwise with stirring. The mixture was heated to reflux temperature and stirred at that temperature for 1½ hours. The mixture was then allowed to cool to room temperature and stirred overnight. Then the reaction mixture was diluted with an equal volume of ethyl ether, and the white solids were separated by filtration and washed with additional ethyl ether. The product was identified as 3-acetylamino-2-iminobenzothiazoline, HBr salt, by infrared and nuclear magnetic resonance analysis, and by elemental microanalysis.

|   | Theoretical | Found |
|---|---|---|
| C | 37.51% | 37.22% |
| H | 3.50 | 3.54 |
| N | 14.58 | 14.40 |

The above product was slurried in 100 ml. of water. The mixture was made neutral with NH₄OH, and the product was recovered by filtration. The product was 3-acetylamino-2-iminobenzothiazoline.

One g. of the above product was dissolved in 50 ml. of acetic acid, and the solution was stirred at reflux temperature for 28 hours. Dioxane was then added, and most of the acetic acid was removed as an azeotrope by distillation. The remaining reaction mixture was poured into a large amount of water, and the aqueous mixture was neutralized with potassium bicarbonate. The mixture was then repeatedly extracted with ethyl acetate, and the ethyl acetate layers were combined and evaporated under vacuum to leave an oil, which partially solidified on standing. The residue was triturated in a 4:1 mixture of ethyl ether-chloroform, and the mixture was filtered. The filtrate was chromatographed on a silica gel column, eluting with a 2:1 mixture of benzene-ethyl acetate. The product-containing fractions were combined and evaporated under vacuum, to produce 2-methyl-s-triazolo[5,1-b]benzothiazole, m.p. 75°–76° C., which was identified by infrared, ultraviolet and nuclear magnetic resonance analysis, mass spectroscopy and elemental microanalysis.

|   | Theoretical | Found |
|---|---|---|
| C | 57.12% | 57.50% |
| H | 3.73 | 4.12 |
| N | 22.21 | 19.08 |

The above synthetic methods are used, with appropriate variations which can be supplied by an ordinarily skilled organic chemist, to produce all of the compounds of this invention, such as the following examples.

EXAMPLE 9
5-methyl-s-triazolo[5,1-b]benzothiazole, m.p. 134°–35° C.

EXAMPLE 10
2,5-dimethyl-s-triazolo[5,1-b]benzothiazole, m.p. 121°–23° C.

EXAMPLE 11
5-fluoro-s-triazolo[5,1-b]benzothiazole, m.p. 165°–67° C.

EXAMPLE 12
5-fluoro-2-methyl-s-triazolo[5,1-b]benzothiazole, m.p. 162°–64° C.

EXAMPLE 13
5-methoxy-s-triazolo[5,1-b]benzothiazole, m.p. 142°–43° C.

EXAMPLE 14
7-methyl-s-triazolo[5,1-b]benzothiazole, m.p. 156°–58° C.

EXAMPLE 15
2,7-dimethyl-s-triazolo[5,1-b]benzothiazole, m.p. 118°–19° C.

EXAMPLE 16
s-triazolo[5,1-b]benzothiazole, m.p. 78°–80° C.

EXAMPLE 17
5-chloro-2-methyl-s-triazolo[5,1-b]benzothiazole, m.p. 263°–64° C.

EXAMPLE 18
5-chloro-2-hydroxy-s-triazolo[5,1-b]benzothiazole, m.p. 340°–41° C. dec.

EXAMPLE 19
5-methoxy-2-methyl-s-triazolo[5,1-b]benzothiazole, m.p. 146°–47° C.

EXAMPLE 20
5-ethyl-s-triazolo[5,1-b]benzothiazole, m.p. 93°–96° C.

EXAMPLE 21
5-ethyl-2-methyl-s-triazolo[5,1-b]benzothiazole, m.p. 95°–96° C.

EXAMPLE 22
2-ethyl-5-methyl-s-triazolo[5,1-b]benzothiazole, m.p. 72° C.

EXAMPLE 23
5-ethyl-2-trifluoromethyl-s-triazolo[5,1-b]benzothiazole, m.p. 77°–78° C.

The compounds described above have been shown in a number of in vivo tests to reduce the adverse effects of both foliar fungi and foliage-consuming insects. The first group of examples below illustrate the tests in which the compounds have been evaluated against fungi.

The compounds were formulated for testing by dissolving or suspending about 3.5 weight percent of each compound in 50:50 acetone-ethanol containing about 10 g./100 ml. of a nonionic surfactant. The solution was then dispersed in deionized water in a quantity such that the water dispersion contained the various compound concentrations indicated in the tables below. Concentrations were measured in parts per million by weight. The compound dispersions were applied to the test plants by spraying them with an air atomizer, using sufficient dispersion to wet the plants thoroughly. Compounds were formulated and applied differently in the bean rust tests, as shown below.

Untreated, infected controls and untreated, normal controls were included in each test. The results are reported on a 1-5 rating scale where 1 indicates severe disease and 5 indicates complete control of the disease. An empty space in the tables shows that the indicated compound was not tested at the indicated rate. In some cases, more than one test was performed against a given phytopathogen, and the results in such cases are reported as averages. Compounds are identified by the example numbers used above.

The following specific test methods were used.

Test 1 helminthosporium leaf spot of wheat

Healthy wheat seed was planted in sterile greenhouse soil. When the seedlings were 4-5 inches tall, they were sprayed with test compound dispersions. The day after treatment, the plants were inoculated with a spore suspension of *Helminthosporium sativum* which had been grown on potato dextrose agar. The plants were placed in a moist growth chamber for two days to start disease growth, and were then transferred to the greenhouse. About a week after treatment, the plants were observed and the results were recorded.

Test 2 late blight of tomato

Four-week-old tomato seedlings were sprayed with aqueous dispersions containing test compounds. The following day, the foliage was inoculated with an aqueous suspension of propagules of *Phytophthora infestans*. The inoculum had been reared on infected wheat seed. The plants were held and observed as described above.

Test 3 powdery mildew of bean

The host plants were 10-day-old bean seedlings. After aqueous dispersions containing test compounds had been sprayed on the foliage of the beans and allowed to dry, the plants were placed in the greenhouse and inoculated by storing them under other bean plants which were heavily infected with powdery mildew (*Erysiphe polygoni*). After about 10 days, the plants were observed and the results recorded as usual.

Test 4 anthracnose of cucumber

Aqueous dispersions containing test compounds were applied to healthy cucumber seedlings grown in sterilized greenhouse soil. The following day, the plants were inoculated with *Colletotrichum lagenarium* conidia as an aqueous suspension. The fungus had been grown on potato dextrose agar in petri dishes. The plants were held in a moist chamber for two days and transferred to the greenhouse, and the disease was observed and rated approximately 12 days after application of the test compounds.

Test 5 rice blast of rice

The test compound dispersions were applied to healthy rice seedlings growing thickly in plastic pots. The plants were inoculated on the next day with *Piricularia oryzae* (grown on rice polish agar) and the plants were held in a moist chamber for two days. The plants were then held in the greenhouse for 5-7 days and observed.

Test 6 bean rust of bean

Pinto bean seedlings were raised in plastic pots in the greenhouse. One week after the seeds were planted, 10 ml. of a 400 ppm. aqueous dispersion of the compound to be tested was added to the soil in which each treated plant was growing, providing a rate of 12.3 kg./ha. The following day, the plants were inoculated with spores of bean rust (*Uromyces phaseoli var. typica*) which were grown on pinto bean plants and applied to the test plants as an aqueous dispersion. The plants were held for two days in a moist chamber, transferred to the greenhouse, and observed about 10 days after inoculation with the phytopathogen.

Test 7 cercospora leaf spot of sugar beet

Sugar beet seedlings were transplanted into square plastic pots and allowed to grow for three weeks. Aqueous dispersions containing the compounds to be tested were sprayed on the leaf surfaces. After the dispersions dried, but within 24 hours, the plants were inoculated with a conidial suspension of *Cercospora beticola* which had been grown on sugar beet leaf decoction agar. After the plants were held in a moist chamber for two days, they were transferred to the greenhouse and observed 2-3 weeks later.

Test 8 botrytis of grape

Sound grape berries were sterilized by immersion in diluted sodium hypochlorite and thoroughly rinsed. The berries were placed on wire screen shelves in compartmented Pyrex plates. The berries were then flamed and sprayed with test chemical dispersions. The following day, the berries were inoculated by spraying 5 ml. of a conidial suspension of *Botrytis cinerea* over each plate containing 12 berries. The inoculum had been grown on frozen lima bean agar. A small amount of water was added to each plate and a cover was sealed over each plate. After 48 hours at 25° C., the berries were observed and disease ratings recorded.

Test 9 apple scab of apple

Apple seedlings at the 4-6 leaf stage were sprayed with aqueous dispersions of the test compounds. The following day, the plants were sprayed with a suspension of fresh conidia of *Venturia inaequalis* obtained from infected apple seedlings kept as a source of inoculum. The plants were held for 2 days in a 20° C. moist chamber to start disease growth and were then transferred to the greenhouse. About 2 weeks after application of the compounds, the plants were observed and the results were recorded.

Test 10 downy mildew of grape

Young expanding grape leaves were detached from healthy vines on the day of the test. Leaves were placed individually in plastic petri dishes, bottom side up, on top of an expanded plastic mat. Water was added to each petri dish, and the petiole of each leaf was wrapped with a water-soaked wad of cotton. Each leaf was sprayed with an aqueous dispersion of the compound to be tested.

After the test compound dispersions had dried, the leaves were inoculated by atomizing a conidial suspension of *Plasmopara viticola* (grown on infected leaf tissue) evenly over the leaf surface. The plates were then covered and were stored in a growth room at about 18° C. and 100% relative humidity where they were exposed to 8 hours a day of artificial light. After about a week of storage, all the leaves were observed and the signs of disease were evaluated.

The following table reports results of testing typical compounds of this invention by the above methods.

acetone-ethanol, and the final aqueous dispersions always contained 0.5 percent of ethanol regardless of the concentrations of the active compound. Compound concentrations of 250, 500 and 1000 ppm. were used.

Rice seed was treated by shaking 20 ml. of Nato rice and 20 ml. of a compound dispersion for 48 hours in a stoppered flask. After the shaking period, the rice seed was drained and thoroughly rinsed with tap water. The seed was planted, and the seedlings were inoculated with *P. oryzae* by spraying the foliage with a *P. oryzae* culture. The inoculated plants were held for two days in a moist chamber and observed.

Test 12 soil surface-applied test

The compounds were formulated as described at the beginning of the test method discussion, and were applied to the soil surface of pots in which 10-cm. rice seedlings were growing. The volume of test compound dispersion was always 75 ml., and rates from 28 kg./ha. to 1.4 kg./ha. were used. Two days after application of Table 1

| Compound of Example No. | Appln. Rate ppm. | Powdery Mildew | Anthracnose | Rice Blast | Botrytis | Bean Rust | Late Blight | Helminthosporium | Apple Scab | Downy Mildew | Cercospora |
|---|---|---|---|---|---|---|---|---|---|---|---|
| 5 | 400 | 1 | 1 | 1 | 1 | 1* | | | | | |
| 6 | 400 | 1 | 1 | 1 | | | | | | | 3 |
| 7 | 400 | 2 | 3.3 | 4.5 | 1 | 1* | 1 | 1 | 1 | 1.8 | 1 |
| | 100 | 1.7 | 1 | 2.7 | | | | | | 1.7 | |
| | 25 | 1.7 | 1 | 1.9 | | | | | | | |
| | 6 | 1 | | 1.8 | | | | | | | |
| 8 | 400 | 1.6 | 1 | 1 | 1 | 1* | | | | | |
| 9 | 400 | 3.5 | 3 | 3.9 | 1 | 1* | | | | 4.3 | |
| | 100 | 1 | 5 | 3.4 | | | | | | 2.3 | |
| | 25 | 1 | 1 | 2 | | | | | | | |
| | 6 | 1 | | 13 | | | | | | | |
| 10 | 400 | 4 | 4 | 1 | 1 | 1* | | | | | |
| | 100 | 1 | 1 | 1 | | | | | | | |
| | 25 | 1 | 1 | 1 | | | | | | | |
| 11 | 400 | 1.2 | 4 | 4.3 | 1 | 1* | | | | 37 | |
| | 100 | 1 | | 3.5 | | | | | | 4.3 | |
| | 25 | 1.3 | 3 | 2.4 | | | | | | | |
| | 6 | 1 | | 2.3 | | | | | | | |
| 12 | 400 | 2 | 3.5 | 2 | 1 | 1* | | | | | |
| | 100 | 1 | 1 | 1 | | | | | | | |
| | 25 | 1 | 1 | 1 | | | | | | | |
| 13 | 400 | 4 | 4 | 1 | 1 | 1* | | | | | |
| 16 | 400 | 1 | 1 | 3.1 | 1 | 1* | | | | 1 | 1 |
| | 100 | 1.7 | | 2.2 | | | | | | 2.3 | |
| | 25 | 1 | | 1.5 | | | | | | | |
| | 6 | 1.7 | | 1.2 | | | | | | | |
| 17 | 400 | 2 | 2.5 | 2 | 1 | 1* | 1 | 1 | 1 | 1 | 1 |
| | 100 | | | 2 | | | | | | | |
| | 25 | | | 2 | | | | | | | |
| | 6 | | | 1 | | | | | | | |
| 18 | 400 | 1 | 1 | 1 | | | | | | | 3 |
| 19 | 400 | 2.5 | 1 | 1 | 1 | 1* | 1 | 1 | 1 | 3 | 1 |
| 20 | 400 | 4.5 | 1 | 1 | 1 | 1* | | | | | 4 |
| 21 | 400 | 5 | 2.5 | 1 | 1 | 1* | | | | | 4 |
| 22 | 400 | 1 | 1 | 1 | 1 | 1* | | | | | |

*12.3 kg./ha.

Typical compounds have also been tested in a system which evaluated the compounds' ability to control rice blast systemically. The compounds were applied either to the soil in which rice plants were grown, or to rice seed, and the extent to which the compound controlled artificially inoculated rice blast was observed.

Test 11 seed soak test

Test compound dispersions were prepared as described above, except that ethanol was used in place of the compounds, the plants were inoculated and held for observation as described in the test method immediately above.

Test 13 soil-incorporated test

Sterile greenhouse soil was treated with the proper amounts of test compounds, dissolved in ethanol, to provide treatment rates from 1.4 to 28 kg./ha. The compounds were thoroughly mixed with the soil in a rotating drum mixer. Rice seed was planted in the treated soil, and the emerged rice seedlings were inoculated and observed as described above.

Seed Soak Treatment

| Compound of Example No. | Appln. Rate ppm. | Disease Rating |
|---|---|---|
| 7 | 1000 | 4.3 |
|  | 500 | 4.3 |
|  | 250 | 3 |
| 9 | 1000 | 3.3 |
|  | 500 | 3 |
|  | 250 | 2.7 |
| 10 | 1000 | 1.3 |
|  | 500 | 1.3 |
|  | 250 | 1.3 |
| 11 | 1000 | 4 |
|  | 500 | 4 |
|  | 250 | 3 |
| 13 | 1000 | 3.3 |
|  | 500 | 1.3 |
|  | 250 | 1 |
| 16 | 1000 | 3 |
|  | 500 | 2.7 |
|  | 250 | 2.3 |
| 17 | 1000 | 2 |
|  | 500 | 1.3 |
|  | 250 | 1.7 |
| 20 | 1000 | 2.3 |
|  | 500 | 2 |
|  | 250 | 2.3 |
| 22 | 1000 | 2.7 |
|  | 500 | 1.7 |
|  | 250 | 1.3 |

Soil Surface Treatment

| Compound of Example No. | Appln. Rate kg./ha. | Disease Rating |
|---|---|---|
| 7 | 5.6 | 4 |
|  | 2.8 | 3.7 |
|  | 1.4 | 3 |
| 9 | 28 | 4.3 |
|  | 14 | 4 |
|  | 7 | 4.3 |
|  | 5.6 | 4.3 |
|  | 2.8 | 3.7 |
|  | 1.4 | 2 |
| 10 | 28 | 1 |
|  | 14 | 1.3 |
|  | 7 | 1.3 |
|  | 5.6 | 5 |
|  | 2.8 | 4.3 |
|  | 1.4 | 3.7 |
| 11 | 28 | 5 |
|  | 14 | 5 |
|  | 7 | 4.3 |
| 13 | 28 | 1.3 |
|  | 14 | 1.7 |
|  | 7 | 1.3 |
| 16 | 28 | 4.3 |
|  | 14 | 5 |
|  | 7 | 4.3 |
|  | 5.6 | 3.7 |
|  | 2.8 | 3 |
|  | 1.4 | 1.2 |
| 20 | 28 | 2.7 |
|  | 14 | 2 |
|  | 7 | 2 |
| 22 | 28 | 1.7 |
|  | 14 | 1 |
|  | 7 | 1 |

Soil Incorporation Treatment

| Compound of Example No. | Appln. Rate kg./ha. | Disease Rating |
|---|---|---|
| 7 | 5.6 | 4 |
|  | 2.8 | 4 |
|  | 1.4 | 1 |
| 9 | 5.6 | 3 |
|  | 2.8 | 1.7 |
|  | 1.4 | 1.3 |
| 11 | 5.6 | 4.3 |
|  | 2.8 | 3.7 |
|  | 1.4 | 2 |
| 13 | 28 | 1.3 |
|  | 7 | 1.3 |
| 16 | 5.6 | 1.7 |
|  | 2.8 | 2 |
|  | 1.4 | 1.7 |
| 20 | 28 | 3 |
|  | 14 | 1 |
|  | 7 | 1.3 |
| 22 | 28 | 2 |
|  | 14 | 2 |
|  | 7 | 1 |

The following examples illustrate tests of typical compounds against insects.

Compounds to be tested were dissolved or suspended in 50:50 acetone-ethanol, and a blend of anionic and nonionic surfactants was added. The solution was then dispersed in water, so that the final dispersion contained about 20 percent of solvent and the concentration of test compound shown in the table below.

The test compound dispersions were sprayed on the foliage of young bean plants in an amount sufficient to wet the foliage completely. The dispersions were then allowed to dry, and individual leaves were removed from the plants. The petiole of each leaf was wrapped in water-soaked cotton, and it was infested with second instar larvae of Mexican bean bettle or third instar larvae of Southern armyworm. Five larvae were applied to each leaf, and two replicates were used for each compound concentration. Mortality was observed on the fourth day after treatment.

Untreated control insects were included with every group of tests.

Insect mortality produced by the comppounds was rated on a rating scale where O represented no mortality, 1 represented less than 50 percent mortality, 2 represented 51-99 percent mortality, and 3 represented 100 percent mortality of the insects. Results were averaged, where a compound was tested repeatedly against an insect. Empty spaces in the table indicate that the compound was not tested at the indicated rate.

The following results were produced by typical compounds of the invention.

| Compound of Example No. | Appln. Rate ppm. | Mexican Bean Beetle | Southern Armyworm |
|---|---|---|---|
| 5 | 1000 | 3 | 0 |
| 6 | 1000 | 0 | 0 |
| 7 | 1000 | 3 | 0 |
|  | 100 | 3 |  |
| 8 | 1000 | 2.5 | 0 |
|  | 100 | 0 | 0 |
| 9 | 1000 | 3 | 0 |
|  | 100 | 3 | 0 |
| 10 | 1000 | 2.5 | 1.5 |
| 11 | 1000 | 2.5 | 0 |
|  | 100 | 0 |  |
| 12 | 1000 | .5 | 0 |
| 13 | 1000 | 3 |  |
|  | 100 | 2.3 | 0 |
|  | 10 | .5 |  |
| 14 | 1000 | 3 | 0 |
| 15 | 1000 | 3 | 0 |
| 16 | 1000 | 3 | 1 |
| 17 | 1000 | 2 | 0 |
| 18 | 1000 | 0 | 0 |
| 19 | 1000 | 0 | 0 |
| 20 | 1000 | 3 | 0 |
|  | 100 | 2 | 0 |
|  | 10 | 0 | 0 |
| 21 | 1000 | 3 | 0 |
| 22 | 1000 | 3 | 0 |
| 23 | 1000 | 3 | 0 |

A systemically-applied test was performed to determine the ability of typical compounds to translocate through plants and to control insects which consume foliage into which the compounds had translocated. The compounds were formulated in solvent with surfactant as described above, and aqueous dispersions containing 200 ppm. of the test compound were prepared. Twenty-five ml. of a dispersion was poured on the soil of each 4-inch square pot, in which bean plants were growing. After 12 hours, a second application of 25 ml. of dispersion was added to each pot. The plants were then held in the greenhouse for 48 hours.

Leaves were removed from the plants, and the cut ends of the petioles were wrapped in water-soaked cotton. Two leaves were placed in a petri dish, and either five third instar Southern armyworm larvae or five second instar Mexican bean beetle larvae were placed in each petri dish. The dishes were closed and held for three days, after which the insect mortality was observed. Untreated control leaves, infested with larvae, were held beside the treated leaves.

It was found that 5-methoxy-s-triazolo[5,1-b]benzothiazole killed 66 percent of the Mexican bean beetle larvae, and that the living larvae were undersized and unable to walk normally. The compound did not kill larvae of the Southern armyworm. Neither Mexican bean beetle nor Southern armyworn larvae were killed by 2-methyl-S-triazolo[5,1-]benzothiazole.

The methods of reducing the adverse effects of plant foliage-attacking fungi, and of reducing the adverse effects of foliage-consuming insects, which are disclosed here are important embodiments of the present invention. In general, both methods are carried out according to the methods and principles which are well known in agricultural chemistry. Detailed discussion of the methods will be provided to assure that agricultural chemists can gain the best advantage from the use of the compounds described herein.

The present method of reducing the adverse effects of plant foliage-attacking fungi comprises contacting the fungi with an effective fungus-inhibiting amount of one of the new compounds of this invention, wherein R represents methyl, hydroxy or hydrogen. The preferred use of the method is in reducing the adverse effects of P. oryzae on rice. The compounds with which the method is preferably carried out are 5-chloro-s-triazolo[5,1-b]benzothiazole, 5-methyl-s-triazole[5,1-b]benzothiazole, 5-fluoro-s-triazolo[5,1-b]benzothiazole, s-triazolo[5,1-b]benzothiazole, and 2,5-dimethyl-s-triazolo[5,1-b]benzothiazole.

Practice of the method need not necessarily kill all of the contacted fungi in order to confer its benefit on the treated plants. Proper use of the method kills part of the fungi, and inhibits another part of the fungi by injuring, or slowing growth of, the organisms. As the data above show, application of a sufficient amount of a compound to inhibit the fungi reduces the adverse effects of the disease, whether all of the fungus population is killed by the compound or not.

As is usual in the plant protection art, best results are obtained by applying the compound several times during the growing season at intervals of from 1 to a few weeks, depending on the weather and the severity of the disease. The methods of formulating the compounds and preparing dispersions of the formulations, and the methods of applying dispersions of the compounds to the plants to be protected, are entirely conventional in the plant protection art. Some explanation of the methods of application will be given merely to assure that those skilled in the art can carry out the invention without undue experimentation.

The compounds can be used for the control of foliage-attacking fungi by either applying the compound to the foliage of the plants, where they directly contact the fungi, or by applying the compounds to the soil, where they are absorbed by the roots of the plants and carried through the plant's tissues to the foliage where they contact the fungi and reduce their adverse effects. Both methods of application are regularly in use in the plant protection art.

It is usual in describing foliar applications of plant protectants to measure the application rate by the concentration of the dispersion in which it is applied. The application rate is measured in this way because it is customary to apply a sufficient amount of the dispersion to cover the foliage with a thin film. The amount of dispersion applied is thus dependent on the foliar area of the plant, and the quantity of plant protecting compound is dependent upon its concentration in the dispersion.

Compound concentrations in the range of from about 25 to about 1500 parts of compound per million parts by weight of the dispersion are used in the practice of the antifungal method of this invention, when the fungi are contacted by applying the compound to the foliage. Of course, from time to time, higher or lower concentrations will be useful, depending on the severity of the infection and the characteristics of the specific compound in use. The named range, however, encloses the usual optimum concentrations of the compounds.

When the method is carried out by applying the compound to the soil in which the plants grow, it is most meaningful to describe the application rate in terms of the amount of compound applied per unit area of soil. Compound application rates in the range of from about 1 to about 50 kg./ha. are used in the practice of this invention to reduce the adverse effects of foliage-attacking fungi. As previously described, application rates higher and lower than the named range will at times be useful.

The present method of reducing the adverse effects of foliage-consuming insects comprises contacting the insects with an insect-inhibiting amount of one of the new compounds of this invention, wherein R represents methyl, ethyl, trifluoromethyl or hydrogen, provided that when R represents a group other than hydrogen, $R^1$ represents hydrogen, methyl, ethyl or chloro. It will be understood that foliage-consuming insect larvae are included in the term "insects".

The preferred use of the method is in reducing the adverse effects of the Mexican bean beetle, and the compounds with which the method is preferably carried out are 5-chloro-s-triazolo[5,1-b]benzothiazole, 5-methyl-s-triazolo[5,1-b]benzothiazole, 2,5-dimethyl-s-traizolo[5,1-b]benzothiazole, 5-fluoro-s-triazolo[5,1-b]benzothiazole, s-triazolo[5,1-b]benzothiazole, and 5-methoxy-s-triazolo[5,1-b]benzothiazole.

The compounds control many injurious foliage-consuming insects, and find their best use against the Coleoptera and Lepidoptera orders of insects, which include the beetles and caterpillars. For example, the compounds are used to reduce the adverse effects of insects such as the boll weevil, the cereal leaf beetle, the various flea beetles, the Colorado potato beetle, the grain beetle, the alfalfa weevil, the carpet beetle, the rice weevil, the rose beetle, the plum curculio, the European cabbage worm, the codling moth, the Eastern tent caterpillar, the Western tussock moth, the sorghum webworm, the saltmarsh caterpillar, and the various leafhoppers.

Practice of the method need not necessarily kill all of the insect population in order to benefit the treated plants, as was discussed above in the discussion of the fungicidal method. Application of an effective insect-inhibiting amount of one of the compounds will reduce the adverse effects of the insects, even though only a part of the insect population is killed.

The insecticidal method is carried out by applying the compounds either to the foliage of plants, or to the soil in which the plants grow, and applications are made in the same manner that fungicidal applications of this invention are made. The insecticidal application rates are from about 100 ppm. to about 2000 ppm., for foliar applications, and from about 10 kg./ha. to about 100 kg./ha. for soil applications.

Thus, it is possible to reduce the adverse effects of both plant-attacking fungi and foliage-consuming insects with a single application of one of the compounds which are included in both the insecticidal and fungicidal method. Such compounds are those wherein R represents methyl or hydrogen, provided that when R represents methyl, R¹ represents hydrogen, methyl, ethyl or chloro. The rates used for combined fungicidal and insecticidal applications are from about 100 ppm. to about 1500 ppm. for foliar applications and from about 10 kg./ha. to about 50 kg./ha. for soil applications. The above group of compounds which are useful for control of both of such insects and fungi are a particularly preferred embodiment of the invention, and the method of reducing the adverse effects of such insects and fungi which comprises contacting the insects and fungi with an effective fungus-inhibiting and insect-inhibiting amount of such a compound is another particularly preferred embodiment of the invention.

The dispersions in which the compounds are applied to foliage are most often aqueous suspensions or emulsions prepared from concentrated formulations of the compounds. Such water-suspendible or emulsifiable formulations are either solids usually known as wettable powders or liquids usually known as emulsifiable concentrates. Wettable powders comprise an intimate mixture of the active compound, an inert carrier and surfactants. The concentration of the active compound is usually from about 10 percent to about 90 percent by weight. The inert carrier is usually chosen from among the attapulgite clays, the montmorillonite clays, the diatomaceous earths, or the purified silicates. Effective surfactants, comprising from about 0.5 percent to about 10 percent of the wettable powder, are found among the sulfonated lignins, the condensed naphthalenesulfonates, the naphthalenesulfonates, the alkylbenzenesulfonates, the alkyl sulfates, and nonionic surfactants such as ethylene oxide adducts of alkyl phenol.

Typical emulsifiable concentrates of the compounds comprise a convenient concentration of the compound, such as from about 100 to about 500 g. per liter of liquid, dissolved in an inert carrier which is a mixture of water-immiscible organic solvent and emulsifiers. Useful organic solvents include the aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, and complx alcohols such as 2-ethoxyethanol. Suitable emulsifirs for emulsifiable concentrates are chosen from the same types of surfactants used for wettable powders.

Adjuvants are frequently used to improve the ability of the aqueous dispersion to coat and adhere to foliage. Such adjuvants as gums, emulsified polybutenes, cationic surfactants and lignin derivatives can often increase the potency of the method in a specific use.

Less frequently, the compounds are applied in the form of dusts. Agricultural chemical dusts typically comprise the compound in a finely powdered form, dispersed in a powdered inert carrier. Most often, the carrier is a powdered clay, such as pyrophyllite, bentonite, a volcanic deposit, or montmorillonite. Dusts are usually prepared to contain concentrations of the compound at the highest part of the concentration range, such as 1500 ppm., and may contain even more active ingredient.

Dispersions of the compounds are applied to foliage in the usual manners. Low-pressure sprayers, high-pressure sprayers and low-volume air blast equipment are all effective for the application of water-dispersed compounds of the invention. Dust dispersions are readily applied by means of the usual equipment which blows the dust into intimate contact with the foliage.

The same types of dispersions used for application to plant foliage can also be applied to the soil. In addition, the compounds can economically and conveniently be applied to the soil in the form of granular formulations. Such formulations, well known to the agricultural chemical art, are prepared by dispersing the compound on an inert carrier of controlled granular character. Most often, the carrier is a coarsely ground clay, such as attapulgite or kaolin clay, having a particle size in the range of from 0.5 o 3 mm. Such granular formulations are easily applied to the soil with applicators which are specially designed to apply accurately controlled amounts of the granular products to the soil.

I claim:
1. A compound of the formula

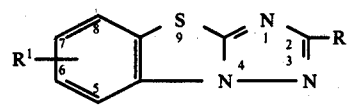

wherein R represents
hydrogen,
hydroxy,
trifluoromethyl,
methyl, or
ethyl;
R¹ represents
hydrogen,
methyl,
ethyl,
chloro,
propyl,
fluoro,
isopropyl,
bromo, or
methoxy;
provided that when R represents ethyl or trifluoromethyl, R¹ represents methyl or ethyl; and provided that methoxy, propyl and isopropyl R¹ groups occupy only the 5-position.

2. The compound of claim 1 which is 2,5-dimethyl-s-triazolo[5,1-b]benzothiazole.

3. A compound of claim 1 wherein R represents hydrogen.

4. The compound of claim 3 which is 5-methoxy-s-triazolo[5,1-b]benzothiazole.

5. A compound of claim 3 wherein $R^1$ represents hydrogen, methyl, ethyl, chloro, or fluoro.

6. The compound of claim 5 which is 5-methyl-s-triazolo[5,1-b]benzothiazole.

7. The compound of claim 5 which is 5-fluoro-s-triazolo[5,1-]benzothiazole.

8. The compound of claim 5 which is s-triazolo[5,1-b]benzothiazole.

9. The compound of claim 5 which is 5-chloro-s-triazolo[5,1-b]benzothiazole.

UNITED STATES PATENT OFFICE
CERTIFICATE OF CORRECTION

Patent No. 4,075,218　　　　　　　　Dated February 21, 1978

Inventor(s) Charles J. Paget

It is certified that error appears in the above-identified patent and that said Letters Patent are hereby corrected as shown below:

Column 1, line 27:　"Triazoles", Hetero." should read
　　　　　　　　　　　--Triazoles", J. Hetero.--.

Column 3, line 39:　"imino-2" should read --amino-2--.

Column 6, line 43:　"[5,1b]" should read --[5,1-b]--.

Column 7, line 36:　"ether-chloroform" should read
　　　　　　　　　　　--ether:chloroform--.

Column 7, line 40:　"benzene-" should read --benzene:--.

Column 8, line 65:　"acetone-ethanol" should read
　　　　　　　　　　　--acetone:ethanol--.

Column 11, Table 1, Compound of Example No. 9, Appln. Rate ppm 6; under heading Rice Blast "13" should read --1.3--.

Column 11, Table 1, Compound of Example No. 11, Appln. Rate ppm 400; under heading Downy Mildew "37" should read --3.7--.

Column 12, line 1:　"acetone-ethanol" should read
　　　　　　　　　　　--acetone:ethanol--.

Column 12, line 3:　"concentrations" should read --concentration--

Column 14, line 4:　"acetone-ethanol" should read
　　　　　　　　　　　--acetone:ethanol--.

Column 14, line 22:　"comppounds" should read --compounds--.

UNITED STATES PATENT OFFICE
CERTIFICATE OF CORRECTION

Patent No. 4,075,218            Dated February 21, 1978

Inventor(s) Charles J. Paget

It is certified that error appears in the above-identified patent and that said Letters Patent are hereby corrected as shown below:

Column 15, line 20: "armyworn" should read --armyworm--.

Column 15, line 21: "2-methyl-S-triazolo[5,1-]benzothiazole" should read --2-methyl-s-triazolo-[5,1-b]benzothiazole--.

Column 17, line 63: "emulsifirs" should read --emulsifiers--.

Column 18, line 30: "0.5 o 3" should read --0.5 to 3--.

Column 20, line 2: "[5,1-]benzothiazole" should read --[5,1-b]benzothiazole--.

Signed and Sealed this

Eighth Day of August 1978

[SEAL]

Attest:

RUTH C. MASON  
Attesting Officer

DONALD W. BANNER  
Commissioner of Patents and Trademarks